(12) United States Patent
Imai et al.

(10) Patent No.: US 7,264,793 B2
(45) Date of Patent: Sep. 4, 2007

(54) NUMB PROTEIN EXPRESSION INHIBITORS BY MUSASHI

(75) Inventors: Takao Imai, Tokyo (JP); Akinori Tokunaga, Tokyo (JP); Tetsu Yoshida, Tokyo (JP); Katsuhiko Mikoshiba, Tokyo (JP); Masato Nakafuku, Tokyo (JP); Hideyuki Okano, Tokyo (JP)

(73) Assignee: Japan Science and Technology Corporation, Kawaguchi-shi (JP)

( * ) Notice: Subject to any disclaimer, the term of this patent is extended or adjusted under 35 U.S.C. 154(b) by 349 days.

(21) Appl. No.: 10/343,311

(22) PCT Filed: Nov. 22, 2001

(86) PCT No.: PCT/JP01/10231

§ 371 (c)(1),
(2), (4) Date: Aug. 21, 2003

(87) PCT Pub. No.: WO02/099102

PCT Pub. Date: Dec. 12, 2002

(65) Prior Publication Data

US 2004/0054140 A1    Mar. 18, 2004

(30) Foreign Application Priority Data

May 31, 2001    (JP) .............................. 2001-164412

(51) Int. Cl.
*A61K 49/00* (2006.01)
*A61K 38/00* (2006.01)
*C12P 21/06* (2006.01)
*C12N 5/00* (2006.01)
*C12N 15/00* (2006.01)
*C12N 15/63* (2006.01)

(52) U.S. Cl. .......................... 424/9.1; 514/2; 435/69.1; 435/320.1; 435/325; 435/455

(58) Field of Classification Search ............... 435/69.1, 435/320.1, 325; 530/350; 424/9.2, 93.1; 514/2, 44
See application file for complete search history.

(56) References Cited

OTHER PUBLICATIONS

Good et al Genomics 52:382-384, 1998.*
Sakakibara et al Dev. Biol. 176:230-242, 1996.*
Hirota et al (Mechanism of Development 87:93-101, 1999.*
Juengst BMJ, 326:1410-11, 2003.*
Check NATURE 422:7, 2003.*
Couzin et al, SCIENCE 307:1028, 2005.*
Rosenberg et al, SCIENCE 287:1751, 2000.*
Anderson, NATURE 392:25-30, 1998.*
Okano H et al, Function of RNA-binding protein Musashi-1 in stem cells. Exp Cell Res. 306(2):349-356. 2005.*
T. Imai et al.: "The neural RNA-binding protein musashi translationally regulates mammalian numb gene expression by interacting with its RNA" BIOLOGY, vol. 21, No. 12, pp. 3888-3900 Jun. 2001.
M. Okabe et al.; "Translational repression determines a neuronal potential in drosophila asymmetric cell division" NATURE, vol. 411, pp. 94-98 May 3, 2001.
A.J. Knoblich et al.: "The N terminus of the drosophila numb protein directs membrane association and actin-dependent asymmetric localization" Proc. Natl. Acad. Sci. USA, 1997.
Wakamatsu et al. NUERON, vol. 23, pp. 71-81 1999.
Ohtsuka et al. EMBO J., vol. 18, pp. 2196-2207 1999.
Nakamura et al. J. NEUROSCI., vol. 20, pp. 283-293 2000.
Artavanis-Tsakanos et al. SCIENCE, vol. 268, pp. 770-776 1999.
Wakamatsu, Y., et al., "NUMB Localizes in the Basal Cortex of Mitotic Avian Neuroepithelial Cells and Modulates Neuronal Differentation by Binding to NOTCH-1," Neuron, vol. 23, May 1999, pp. 71-81.
Ohtsuka, T., et al., "Hes1 and Hes 5 as Notch Effectors in Mammalian Neuronal Differentiation," The EMBO Journal, vol. 18, No. 8, 1999, pp. 2196-2207.
Nakamura, Y., et al., "The bHLH Gene Hes1 as a Repressor of the Neuronal Commitment of CNS Stem Cells," The Journal of Neuiroscience, Jan. 1, 2000, pp. 283-293.
Artavanis-Tsadonas, S., et al, "Notching Signaling: Cell Fate Control and Signal Integration in Development," Science, vol. 284, Apr. 30, 1999, pp. 770-776.

* cited by examiner

*Primary Examiner*—Sumesh Kaushal
(74) *Attorney, Agent, or Firm*—Oblon, Spivak, McClelland, Maier & Neustadt, P.C.

(57) ABSTRACT

An Numb protein expression inhibitor comprising, as active ingredient, Musashi protein, a polypeptide having an amino acid sequence obtained by replacement, deletion, addition or insertion of at least one amino acid in an amino acid sequence of Musashi protein, or a gene encoding said polypeptide.

By the present invention, a new function of Musashi protein has been elucidated. Described specifically, Musashi protein inhibits expression of Numb protein having a neuronal differentiation regulating function and potentiates the activity of the Notch signaling system, so that Musashi protein can be used as a therapeutic for various diseases of the central nervous system.

9 Claims, 11 Drawing Sheets

Effecter wildtype msi1 or mutated msi1

Reporter or or

NUMB PROTEIN EXPRESSION INHIBITORS BY MUSASHI

TECHNICAL FIELD

This invention relates to drugs, which are useful as therapeutics for diseases caused by disorders of the Notch signaling system and also as potentiators of neural stem cell proliferation activity by the molecular mechanisms to inhibit expression of Numb protein, a neuronal differentiation regulating factor which antagonizes the Notch signaling.

BACKGROUND ART

Numb protein (Wakamatsu et al., Neuron, 23, 71-81, 1999) is known to inhibit the signaling cascade of Notch protein which is required for the self-renewing activity of mammalian central neural stem cells (Ohtsuka et al., EMBO J., 18, 2196-2207, 1999; Nakamura et al., J. Neurosci., 20, 283-293, 2000).

Further, a Notch-protein-mediated signaling system takes part in the self-renewal, survival and/or the status of neural stem cells (Artavanis-Tsakanos et al., Science, 268, 770-776, 1999).

DISCLOSURE OF THE INVENTION

Musashi protein is known to be preferentially expressed in stem cells of the mammalian neural nervous system. The present inventors proceeded with an investigation on its function. As a result, the present inventors found that Musashi protein represses expression of Numb protein at the level of its translation and further that it has activity to potentiate Notch signaling activity and is useful as therapeutics for diseases caused by disorders of the Notch signaling activity. In order to study the in vivo function of Musashi, the present inventors also proceeded with an investigation on animals in which the Musashi gene had been deleted. As a result, it was also found that Musashi protein potentiates the proliferation activity of neural stem cells. These findings have led to the completion of the present invention.

Described specifically, the present invention provides an Numb protein expression inhibitor comprising, as active ingredient, Musashi protein, a polypeptide having an amino acid sequence obtained by replacement, deletion, addition or insertion of at least one amino acid in an amino acid sequence of Musashi protein, or a gene encoding the polypeptide.

The present invention also provides a Notch signaling activity potentiator comprising, as active ingredient, Musashi protein, a polypeptide having an amino acid sequence obtained by replacement, deletion, addition or insertion of at least one amino acid in an amino acid sequence of Musashi protein, or a gene encoding the polypeptide.

The present invention also provides a neural stem cell proliferation activity potentiator comprising, as active ingredient, Musashi protein, a polypeptide having an amino acid sequence obtained by replacement, deletion, addition or insertion of at least one amino acid in an amino acid sequence of Musashi protein, or a gene encoding the polypeptide.

The present invention also provides a method for inhibiting expression of Numb protein, which comprises applying an effective amount of Musashi protein, a polypeptide having an amino acid sequence obtained by replacement, deletion, addition or insertion of at least one amino acid in an amino acid sequence of Musashi protein, or a gene encoding the polypeptide.

The present invention further provides a method for potentiating Notch signaling activity, which comprises applying an effective amount of Musashi protein, a polypeptide having an amino acid sequence obtained by replacement, deletion, addition or insertion of at least one amino acid in an amino acid sequence of Musashi protein, or a gene encoding the polypeptide.

The present invention further provides a method for potentiating neural stem cell proliferating activity, which comprises applying an effective amount of Musashi protein, a polypeptide having an amino acid sequence obtained by replacement, deletion, addition or insertion of at least one amino acid in an amino acid sequence of Musashi protein, or a gene encoding the polypeptide.

Additionally, the present invention further provides use of Musashi protein, a polypeptide having an amino acid sequence obtained by replacement, deletion, addition or insertion of at least one amino acid in an amino acid sequence of Musashi protein, or a gene encoding the polypeptide for the production of an Numb protein expression inhibitor.

The present invention still further provides use of Musashi protein, a polypeptide having an amino acid sequence obtained by replacement, deletion, addition or insertion of at least one amino acid in an amino acid sequence of Musashi protein, or a gene encoding the polypeptide for the production of a Notch signaling activity potentiator.

The present invention yet further provides use of Musashi protein, a polypeptide having an amino acid sequence obtained by replacement, deletion, addition or insertion of at least one amino acid in an amino acid sequence of Musashi protein, or a gene encoding the polypeptide for the production of a neural stem cell proliferation activity potentiator.

BEST MODE FOR CARRYING OUT THE INVENTION

Figure 1:
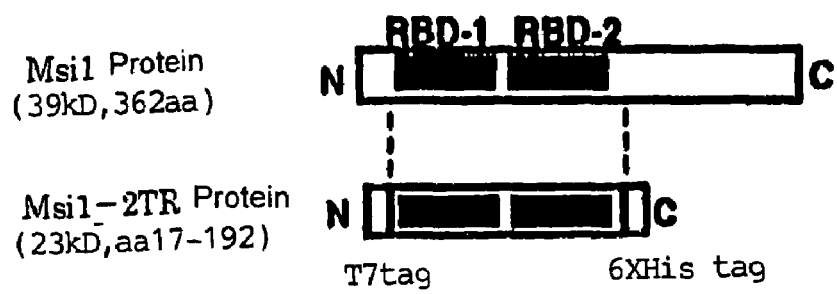
FIG. 1 is a schematic representation of the domain structures of full-length Msi1 protein and a bacterially expressed Msi1 fusion protein Msi1-2TR, which was used for the selection of high affinity RNA sequences to which Msi1 would bind.

Musashi protein, an active ingredient in drugs according to the present invention, is an RNA-binding protein which is preferentially expressed in mammalian CNS stem cells. Musashi protein is fairly known to include Musashi1 (Msi1) and Musashi2 (Msi2) (Sakakibara, S. et al., Dev. Biol., 176, 230-242, 1996). Of these Musashi subfamily proteins, Musashi1 (Msi1) (SEQ ID NO: 17) is particularly preferred.

Because genes encoding these Musashi subfamily proteins have already been cloned, these Musashi subfamily proteins may be prepared by DNA recombination technology, specifically by using cells transfected with expression vectors including the cloned genes, although they can be isolated from cells in which they exist.

Musashi protein may be the protein itself expressed in neural stem cells, or as an alternative, one obtained by modifying its amino acid sequence at a part thereof insofar as the modified protein retains similar properties. It is also possible to use, for example, a polypeptide having an amino acid sequence obtained by replacement, deletion, addition of insertion of at least one amino acid in the amino acid sequence of Musashi protein. No particular limitations are imposed on the degree and position of such a replacement, deletion, addition or insertion insofar as the modified amino acid sequence has properties similar to Musashi protein. Like Musashi protein, these modified polypeptides can also be prepared by DNA recombination technology.

As a further alternative, a gene which encodes Musashi protein or the modified polypeptide may be administered in vivo to make the protein or modified polypeptide.

As will be demonstrated in examples to be described subsequently herein, Musashi protein binds mRNA of a mammalian numb gene, regulates the expression of the numb protein at the level of its translation.

As a result of regulation of the expression of Numb protein by the expression of Musashi protein, Notch signaling activity is potentiated. Accordingly, Musashi protein is useful as therapeutics for diseases caused by disorders of the Notch signaling activity, specifically for self-renewal and/or inviability of neural stem cells.

Musashi protein also potentiates proliferation activity of neural stem cells, because in neural stem cells derived from an Msi1-deficient mouse, the neurosphere forming ability is substantially reduced when the expression of Msi2 gene is repressed.

In the present invention, each subject to which Musashi protein or its gene is applied may be any one of cells, tissues and animals including human being.

To administer a drug according to the present invention to animals including human being, especially to mammals, the above-described active ingredient can be formulated together with a pharmaceutically acceptable carrier into drug compositions of various dosage forms. As such dosage forms, injections are preferred. Examples of the pharmaceutically acceptable carrier can include distilled water, solubilizers, stabilizers, emulsifiers, and buffering agents. The dosage of such a drug may range from 0.1 µg to 10 mg or so per day in terms of the weight of Musashi protein, although it varies depending upon the disease, sex, body weight and the like.

EXAMPLES

The present invention will next be described in detail based on the following examples, which are by no means intended to limit the present invention.

Example 1

A. Materials and Methods (1) Preparation of Msi1 Fusion Protein

To prepare mouse Msi1 fusion protein (Msi1-2TR), a plasmid vector, pET21a-msi12TR, was constructed by inserting a part of the coding region (corresponding to aa 7 to 192) of the musashi-1 cDNA into the pET21a expression vector (Novagene). The plasmid was introduced into *Escherichia coli* strain BL21/(DE3) pLysS, followed by amplification. The expression and affinity purification of the fusion protein were performed by methods reported in a technical paper (Kaneko et al., Dev. Neurosci., 22, 138-152, 2000).

(2) Selection of Msi1 RNA Ligands

RNA selection was basically performed according to methods reported in technical papers (Buckanovich et al., Mol. Cell. Biol., 17, 1197-1204, 1997; Tsai et al., Nucleic Acids Res. 19, 493 1-4936, 1991). Oligonucleotides harboring a 50-bp random sequence surrounded by primer binding sites (5'-GGGAAGATCTCGACCAGAAG-$N_{50}$-TATGTGGGTCTACATGGATCCTCA-3'; SEQ ID NO: 19) were synthesized using a DNA synthesizer (Nissinbo). The oligonucleotides were amplified by PCR using a forward primer containing the T7 promoter sequence and a reverse primer (forward primer: 5'-CGAATTCTAATACGACTCACTATAGGGAAGATCTCGACCAGAAG-3'; SEQ ID NO: 1; reverse primer: 5'-TGAGGATCCATGTAGACGCACATA-3': SEQ ID NO: 2). The library DNAs were transcribed in vitro with T7 RNA polymerase and [α-$^{32}$P]UTP (Amersham Pharmacia Biotech). The resulting RNA was applied to a column which was filled with nickel affinity resin. The column had been preadsorbed with 100 µg of purified histidine-tagged Msi1 fusion protein. As binding buffer, 0.5 M LiCl, 20 mM Tris-HCl [pH 7.5 ] and 1 mM $MgCl_2$ were used. The beads were then washed with 10 ml of binding buffer. Bound RNA was eluted from the column in elution buffer (20 mM Tris-HCl [pH 7.5], 1 M imidazole), phenol extracted, and ethanol precipitated. The RNA was reverse transcribed with Moloney murine leukemia virus reverse transcriptase (Gibco BRL), the resulting cDNA was used for PCR. Using the forward and reverse primers given above, the DNA was amplified under the following conditions: 15 cycles of 1 min at 94° C., 1 min at 59° C., and 1 min at 72° C. The PCR product was used for the next round in the selection procedure. This process was repeated an addition seven times before the products were subcloned into the pUC 119 vector (Clontech). RNA secondary structure was predicted using the commercial sequence analysis software DNASIS (Hitachi Software Engineering Inc.) program based on the Zuker-Siegler method.

(3) Gel Shift Assays

Gel shift assays were performed with various amounts of Msi1 fusion protein in 16 µl of KNET buffer (Levine et al., Mol. Cell. Biol. 13, 3494-3504, 1993). Ten thousand counts per minute (approximately 4 fmol) of selected $^{32}$P-labeled RNA ligand (S8-13 and S8-19) was added to the solutions containing Msi1 fusion protein. For the competition experiment, unlabeled RNA was added before the $^{32}$P-labeled RNA. Protein and RNA samples were allowed to equilibrate for 30 min at room temperature. After incubation, the mixtures were immediately loaded onto 8 to 15% polyacrylamide gels (0.5× Tris-borate-EDTA buffer, 5% glycol) and fractionated by electrophoresis. The gels were then dried and exposed to XAR autoradiography film (Kodak).

(4) In Vitro Binding Assay Using m-numb 3'UTR

[$^{35}$S]methionine-labeled full-length Msi1 protein was prepared by an in vitro transcription translation system using the pRSETb-msi1 plasmid vector (Sakakibara et al., Dev. Biol. 176, 230-242, 1996). pET21a-msi12TR, pRSETb-C17 (C-terminal half), and reticulocyte lysate containing T7 RNA polymerase (Promega). The Msi1 protein was incubated with m-numb RNAs labeled with biotin-14-CTP in binding buffer (150 mM NaCl, 50 mM Tris-HCl [pH 8.0], 0.05% NP-40, 0.1% sodium azide) for 30 min. The mixture of Msi1 and m-numb RNA was then added to streptavidin-agarose beads previous resuspended in binding buffer. The beads were then washed with 1 ml of binding buffer five times. The bead pellet was resuspended in sodium dodecyl sulfate-polyacrylamide gel electrophoresis (SDS-PAGE) loading buffer, boiled for 5 min, and spun. The supernatant was loaded onto a 15% SDS-polyacrylamide gel and fractionated by electrophoresis. After electrophoresis, the gel was dried and exposed to Fuji RX-U film at −80° C. for 1.5 to 8 h.

(5) Cell Culture and in Vivo Binding Assay

NIH 3T3 cells were cultured in Dulbecco's modified Eagle's medium (Nissui) supplemented with 10% calf serum. NIH 3T3 cells were plated onto 60-min dishes (Falcon) ($10^6$ cells/dish). On the following day, cells were transfected with 1 µg of the Msi1 expression constructs (pcDNA3-FLAGMsi1HAT, pcDNA3-FLAGMsi1mutR1HAT, and pcDNA3-FLAGMsi1) shown in FIG. 11, using the Effective transfection reagent) (Qiagen). Two days later, the transfected cells were suspended in 1 ml of NET-Triton buffer, homogenized, and spun in a microcentrifuge. In the presence of RNase inhibitor (0.5 U/µl) (Promega), histidine affinity tag (HAT)-tagged Msi1-RNA complexes in the supematants were pulled down by Talon resin (Clontech). Extraction of precipitated RNA, DNase I treatment, and reverse transcription was performed (Buckanovich et al., Mol. Cell. Biol., 17, 3194-3201, 1999). Subsequently, PCR was performed with rn-numb gene-specific primers using 32 cycles of 30 s at 94° C., 30 s at 60° C., and 30 s at 72° C. or with β-actin-specific primers using 25 cycles of 30 s at 94° C., 30 s at 60° C., and 30 s at 72° C. Primers used in the PCR were as follows: the m-numb primer set, 5'-ATGAGCAAGCAGTGTTGCCTGG-3' (SEQ ID NO: 3) and 5'-CAAGTAGCTGCAACTGGCTGG-3' (SEQ ID NO: 4); and β-actin, 5'-CTTCCTCCCTGGAGAA- GAGCTATGAGC-3' (SEQ ID NO: 5) and 5'-GCCTA-GAAGCACTTGCGGTGCACG-3' (SEQ ID NO: 6).

(6) Reporter Assay Using Luciferase and Quantification of Reporter mRNA by Northern ELISA System NIH 3T3 cells ($3\times10^5$ cells/ml per assay) were transfected with 0.2 μg of firefly luciferase reporter vector, 20 ng of Renilla luciferase control vector pRL-TK (Toyo Ink), and 0.3 μg pEGFP-N3 vector (Clontech) and with a combination of pcDNA3 vector (Invitrogen) and pCDNA3-T7Msi1 or pCDNA3-T7Msi1mutR1 expression vector (totaling 1.5 μg), using Fugene 6 transfection reagent (Roche). After 2 days of incubation, the cells were lysed with luciferase assay lysis buffer (Toyo Ink). The firefly luciferase (reporter) activities and Renilla luciferase activities(control) were measured with individual reaction substrate mixtures supplied by the manufacturer using a Berthold Lumat LB9507 luminometer. The ratio of reporter luciferase activity in relative light units was divided by the control Renilla luciferase activity to give a normalized reporter luciferase value.

NIH 3T3 cells were transfected and cultured as described above for the reporter assay. Two days after, cells were harvested, and total RNA was extracted from each NIH 3T3 cell with Trizol reagent (Gibco BRL). After DNase I treatment, RNAs (2 μg each) were used for quantification of reporter luciferase RNA and enhanced green fluorescent protein (EGFP) RNA as a control by a Northern enzyme-linked immunosorbent assay (ELISA) system (Rosh Diagnostics). Digoxigenin-labeled detection probes were prepared following PCR amplification using digoxigenin-11-2'-deoxy-uridine-triphosphate as a substrate and 10 ng of plasmid DNA (pGV-P2; Promega, and pEGFP-N3; C.lontech) as templates. PCRs were performed using 25 cycles of 94° C. for 30 s, 52° C. for 30 s, and 72° C. for 30 s, with a final extension phase of 2 min, using Ex Taq DNA polymerase (Takara), luciferase gene-specific primers, and EGFP-specific primers as follows: luciferase forward primer, 5'-GAGGTCCTATGATTATGTCCGG-3'(SEQ ID NO: 7); luciferase reverse primer, 5'-GTTGGAGCAA-GATGGATTCC-3'(SEQ ID NO: 8); EGFP forward primer, 5'-CAGAAGAACGGCATCAAGG-3'(SEQ ID NO: 9); and EGFP reverse primer, 5'-TGCTCAGGTAGTGGTTGTGG-3'(SEQ ID NO: 10). The expression levels of luciferase-m-numb 3'-UTR chimeric mRNA versus those of control EGFP mRNA in NIH 3T3 cells were determined from the photometric intensity (measured of absorbance at 450 nm) with peroxidase and 3,3',5,5'-tetramethylbenzidine.

(7) Preparation of Recombinant Adenovirus and Infection Experiment

The recombinant adenovirus Adex-FLAGMsi1 was generated using the pAdex1pCAw vector. Procedure was substantially as reported in a technical paper (Hashimoto et al., Hum. Gene Ther., 7, 149-158, 1996). The high-titer recombinant adenovirus stock (Adex-FLAGMsi1, $3\times10^{10}$ PFU/ml; Adex-NLLacZ, $3\times10^{10}$ PFU/ml) was obtained and stored at −80° C.

NIH 3T3 cells ($2.5\times10^6$ cells) were infected with 1,000-fold-diluted adenovirus solution in 5 ml of Dulbecco's modified Eagle's medium containing 5% fetal bovine serum. Two days later, the cells were lysed by lysis buffer (Buckanovich et al., Mol. Cell. Boil., 17, 3194-3201, 1999) and used in Western blotting analysis (Kaneko et al., Dev. Neurosci., 22, 138-152, 2000), Northern blot analysis, and sucrose gradient centrifugation analysis. Affinity-purified rabbit polyclonal antibody against chick Numb (Wakamatsu et al., Neuron, 23, 71-81, 1999) that recognizes the amino acid sequence which is perfectly conserved between the mouse and chicken proteins as an epitope, anti-FLAG-M2 mouse monoclonal antibody (Sigma), and antitubulin mouse monoclonal antibody (Sigma clone no. 1A2) were used at 1:500, 1:1,000 and 1:1,000 dilutions, respectively, for immunoblots in 3% skim milk phosphate-buffered saline. Each immunoreactivity was detected by diaminobenzidine. Signals were quantified using the NIH Image program (version 1.62, NIH).

(8) RNA Quantification by Northern Blot Analysis

Total RNAs were extracted with Trizol reagent (Gibco BRL) from NIH 3T3 cells infected with Adex-FLAGMsi1 by the above-described method and precipitated with ethanol. The RNAs were loaded onto morpholinepropane-sulfonic acid-formaldehyde-agarose gels and then transferred to a Hybond N+ nylon membrane (Amersham Pharmacia Biotech) and probed with $^{32}$P-labeled m-numb cDNA and β-actin DNA. Hybridization signals were detected with XAR autoradiography film (Kodak) and quantified using BAS5000 (Fuji). The ratio of hybridization signals for m-numb mRNA over those for β-actin mRNA yielded normalized quantities of m-numb mRNA level. Two independent experiments were performed, and the average value was calculated.

(9) Sucrose Gradient Centrifugation

Sucrose gradient centrifugation was performed by a method reported in a technical paper (Siomi et al., Mol. Cell. Biol. 16, 3825-3832, 1996). NIH 3T3 cells infected with Adex-FLAGMsi1 as described above were harvested by centrifugation, washed with cold phosphate-buffered saline, resuspended in buffer A (10 mM potassium acetate, 2 mM magnesium acetate, 1 mM dithiothreitol, 5 mM HEPES [pH 7.3], 2 μg of leipeptin per ml, 2 μg of pepstatin per ml, and 0.5% aprotinin), incubated on ice for 10 min, and disrupted by passage through needles. Centrifugation at 2,500×g for 10 min yielded a pellet and a supernatant fraction designated cytoplasmic lysate. The KCl concentration was adjusted to 100 mM at this point. Cytoplasmic lysate was resolved on a linear sucrose gradient (5 to 30%) containing 100 mM KCl, 10 mM potassium acetate, 2 mM magnesium acetate, 1 mM dithiothreitol, 5 mM HEPES [pH 7.3], 2 μg of leipeptin per ml, 2 μg of pepstatin per ml, and 0.5% aprotinin. The gradients were centrifuged at 4° C. in a Hitachi P40St1286 rotor at 40,000 rpm for 150 min. Following centrifugation, fractions were collected from the top of gradients (300 μl per fraction) using a Piston gradient fractinator (Biocomp, Inc.). Thirty microliters of each fraction was used for Western blotting. RNA was extracted from the fractions with phenol and precipitated with ethanol, and $A_{254}$ was measured.

(10) HES1-Promotor Transactivation Assay

To measure HES1 promoter activity, NIH 3T3 cells were transfected with 0.2 μg of pHES-1p-luciferase (Jarriault et al., Nature, 377, 355-358, 1995) alone, together with 0.025 μg of pEF-BOS-FCDN1 (an expression plasmid for the Notch1 intracellular domain [FCDN1, aa 1747 to 2531]) (Nofziger et al., Development, 126, 1689-1702, 1999), in combination with various amounts of pcDNA3-T7Msi1 or pEF-BOSneo-R218H (Kato et al., Development, 124, 4133-4141, 1997), or in combination with 1 μg of pCDNA3-HAmNumb; 100 ng of SV40-LacZ construct or 20 ng of the Renilla luciferase control vector pRL-TK (Toyo Ink) was include in each transfection as an internal control. Three independent experiments were carried out. Luciferase activity was measured 48 h after transfection in a luminometer Lumat LB9507 (Berthold) and normalized according to β-galactosidase activity or Renilla luciferase activity.

B. Results (1) In Vitro Selection of High-Affinity RNA Ligands for Msi1

Figure 2:
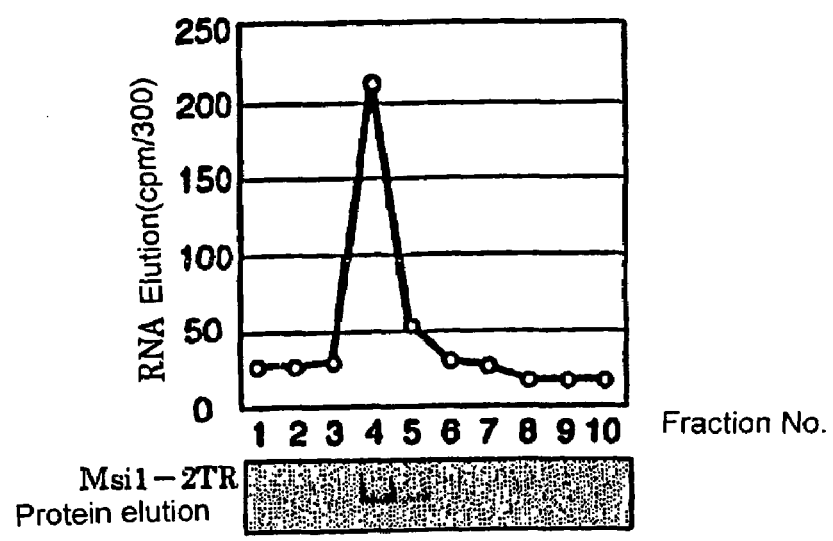
FIG. 2 is a diagram showing the binding of Msi1-2TR protein to RNAs.
Figure 3:
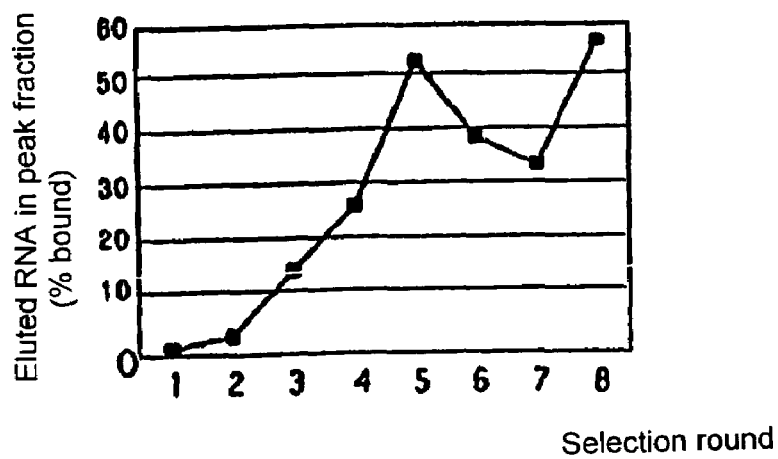
FIG. 3 is a diagram illustrating the percentage of bound RNAs in total RNAs employed in each selection run using radioactivity as an index.

To identify the target RNA sequence of Msi1, an affinity elution-based RNA selection (SELEX) was performed. A $^{32}$P-labeled RNA pool was synthesized in vitro using an PCR-amplified oligonucleotide library of 50-nucleotide semi-complete random sequences as templates. The synthesized RNA pool was then applied to a nickel affinity column to which Msi1 fusion protein Msi1-2TR had been absorbed previously Msi1-2TR contained the two tandem RRM-type (Burd et al., EMBO J., 13, 1197-1204, 1994) RNA-binding domains (RBDs) (aa 17 to 192) as well as the histidine tag at its C terminus and a T7 tag at its N terminus (FIG. 1). After being washed to remove RNAs that did not interact with the Msi1-2TR fusion protein, the Msi1-2TR fusion protein-RNA complexes were eluted in buffer containing 1 M imidazole. The elution profile of the first round of selection is shown in FIG. 1B. The elution of RNA and protein was monitored by counting the radioactivity and by performing SDS-PAGE, respectively (FIG. 2). After each cycle, the bound RNA was extracted and reverse transcribed to the first strand of cDNA using the SELEX reverse primer, and the cDNAs encoding the selected RNA sequences were amplified by PCR and used again as templates to synthesize RNAs for another cycle of binding and amplification. By repeating this affinity RNA-ligand selection, the fraction RNA binding to Msi1 was found to increase from 0.2% in the initial RNA pool to 60% after eight selection cycles (FIG. 3). In this way, there was obtained an RNA pool that was enriched in RNA sequences that preferentially bind to Msi1.

Figure 4:
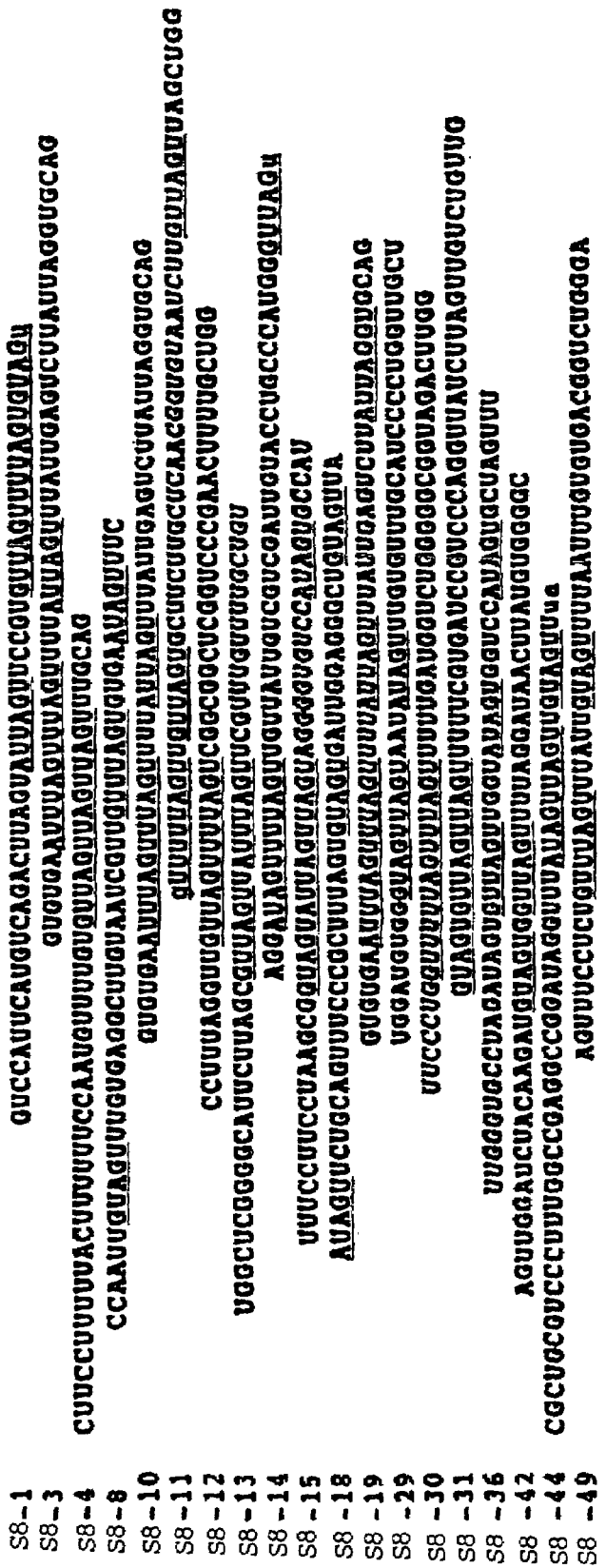
FIG. 4 is listing showing sequences of Msi1-selected RNAs. The sequences designated S8-1 through S8-49 correspond to SEQ ID NOs: 21-39, respectively.
Figure 5:
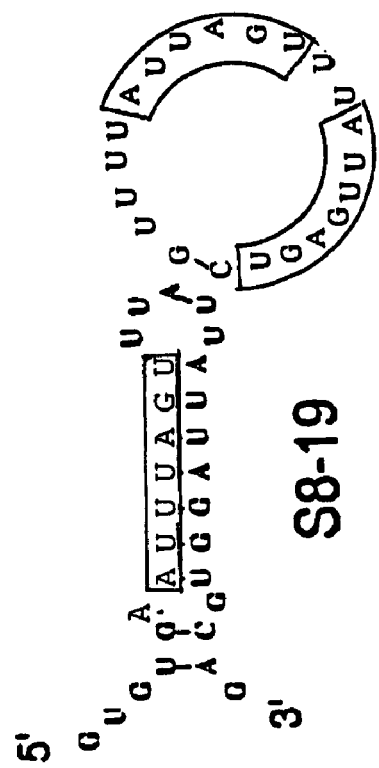
FIG. 5 is a schematic representation of representative secondary structures of the RNA sequences selected by Msi1, in which shading indicates the selected consensus sequences. S8-13 corresponds to SEQ ID NO: 28 and S8-19 corresponds to SEQ ID NO: 32.
Figure 5:
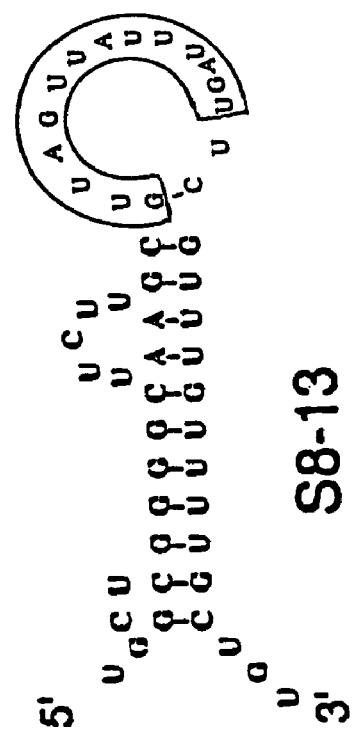

Fifty (50) independent cDNA clones that were obtained after the eight selection cycles were then sequenced, and the information was used to identify the RNA consensus sequence for the binding of Msi1 (FIG. 4). Twenty representative clones are shown in FIG. 4, all of which contained short U stretches, 1 to 6 bases long, that were interrupted by A or AG. The other 30 clones that are not shown also contained sequences that matched this consensus, and some were redundant, containing the same RNA sequence as some of the depicted clones in FIG. 4. In particular, the (G/A)$U_n$AGU motif was seen in most of the selected clones (underlined in FIG. 4, in many cases, n=1 to 3). These uridine-rich sequences were often repeated two or three times. The frequencies of the U number (n) were as follows: n=1, 31%; n=2, 40%; n=3, 21%; n=4, 5%; n=5, 2%. Interestingly, in most cases this sequence element was located in the loop region of a stem-loop structure (FIG. 5). This was predicted using commercial sequence analysis software based on Zuker-Stiegler method (DNasis; Hitachi Software Engineering Inc.).

(2) RNA-Protein Binding Experiments

Figure 6:
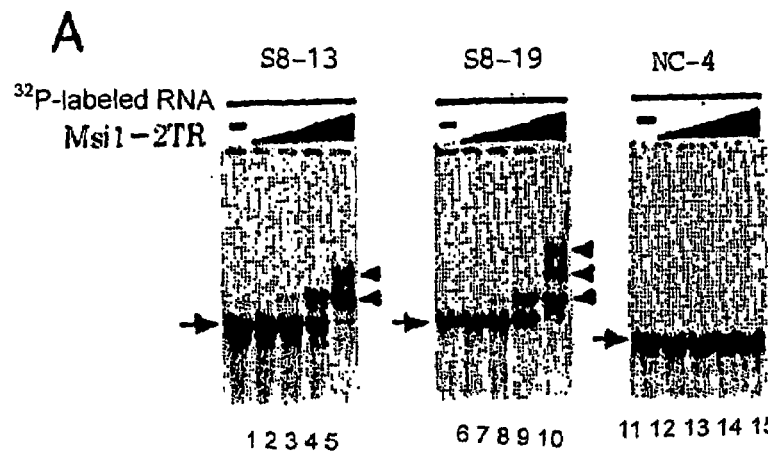
FIG. 6 illustrates (A) the results of gel shift assays of Msi1 protein [0 fmol (lanes 1, 6 and 11), 1 fmol (lanes 2, 7 and 12), 10 fmol (lanes 3, 8 and 13), 100 fmol (lanes 4, 9 and 14), 1000 fmol (lanes 5, 10 and 15)] and (B) the results of competitive RNA-binding experiments conducted using unlabeled RNAs [4 fmol of labeled RNA was incubated without (lanes 16, 21, 26 and 31) or with 10 fmol of Msi1-2TR protein and the following amounts of unlabeled RNA: 0 fmol (lanes 17, 22, 27 and 32), 40 fmol (lanes 18, 23, 28 and 33), 400 fmol (lanes 19, 24, 29 and 34), and 4,000 fmol (lanes 20, 25, 30 and 35)]

To further investigate whether the repeated (G/A)$U_n$AGU motif is an essential sequence element for the Msi1-RNA interaction, binding assays were performed using the Msi1-2TR fusion protein and RNA sequences derived from the most frequently selected clones, S8-13 and S8-19, which contain, respectively, two and three copies of sequences that match the selected consensus motif (FIG. 6A). Gel shift analysis was performed by incubating 4 fmol of labeled RNAs with various amounts of Msi1-2TR protein. The number of retarded bands in each experiment corresponded to the number of the sequences that matched the consensus sequence motif, (G/A)$U_n$AGU, within a selected clone. S8-13 RNA contains two consensus motifs, and S8-19 RNA has three motifs. Msi1 protein did not recognize the RNA-designated NC-4, which does not contain the selected consensus sequence (FIG. 6A). To examine whether the Msi1 protein bound specifically to the selected RNA, competitive binding assays were preformed with unlabeled RNA containing the Msi1 selected-consensus sequence or a nonspecific competitor that did not contain the full consensus sequence (FIG. 6B). Four femtomoles of $^{32}$P-labeled RNA (S8-13 or S8-19) was incubated with 100 fmol of Msi1 protein and a 10-, 100-, or 1000-fold excess of unlabeled RNA, followed by gel shift analysis (FIG. 6B, lanes 13 to 15, lanes 18 to 20, lanes 23 to 25, and lanes 28 to 30, respectively). The intensities of the retarded bands representing the protein-RNA complex were decreased by the addition of excess unlabeled RNA containing the Msi1 recognition sequence (i.e., the same sequence as the labeled RNA) as a specific competitor. However, the intensities were not decreased by the addition of RNA that did not contain the Msi1 recognition sequence (NC-4). These observations indicated that the Msi1 protein specifically recognized the RNAs containing the sequence that matched the consensus sequences selected in vitro. The binding affinities of the selected RNA sequences to Msi1 were determined based on the intensity of the regarded band representing RNA-Msi1 complex in the gel retardation assays. The dissociation constant $K_d$ is equal to the protein concentration at which 50% of RNA is bound. In FIG. 6A, lane 4 and lane 9, 50% of RNA was bound to protein as determined by densitometry evaluation. $K_d$ was calculated to be about 4 nM for S8-13 and S8-19. Thus, Msi1 was shown to bind to the RNA containing the sequences that match the consensus sequence motifs with high affinity.

(3) Binding of Msi1 to m-numb mRNA both In Vitro and in Vivo

Candidates for downstream target genes of the Msi1 protein were explored based on the results of the in vitro selection experiments. Since Msi1 is preferentially expressed in undifferentiated neuronal progenitor cells, mRNAs of genes regulating neural differentiation (either positively or negatively) may be possible downstream targets of Msi1. Then, m-numb, which encodes a Notch antagonist is a likely candidate for an Msi1 target gene, based on the following facts. First, the 3'-untranslated region (UTR) of m-numb mRNA contains the consensus sequence motif for Msi1 binding. Second, the region of m-numb gene expression overlaps that of msi1 expression in neuroepithelial cells in the ventricular zone of the neural tube. Third, m-numb is involved in the regulation of neuronal differentiation.

Figure 7:
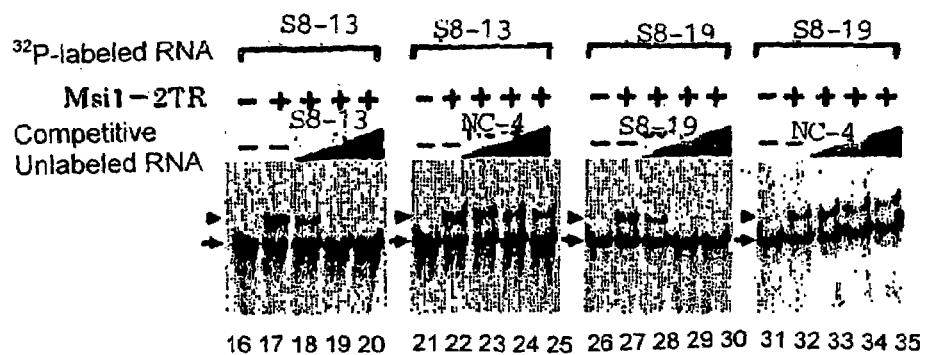
FIG. 7 is a schematic representation of the structure of numb gene, in which the arrows (N1, N2 and N3) indicate regions that were individually transcribed in vitro while the vertical arrowhead indicates a region containing a putative Msi1-binding sequence (UAGGUAGUAGUUUUA; SEQ ID NO: 20)
Figure 8:
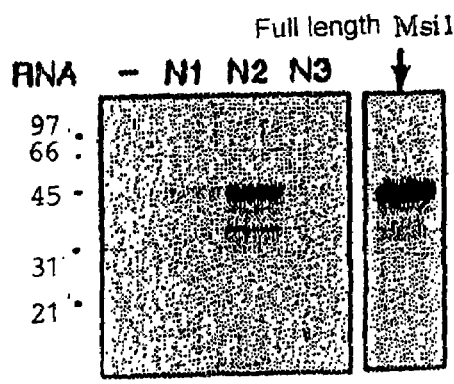
FIG. 8 depicts the results of binding assays of the Msi1 protein to various transcripts derived from the 3'-UTR of m-numb mRNA, in which N1 and N3 indicate RNAs of m-numb gene, (−) designates of a lane for the absence biotin-labeled RNA, and the rectangle on the right photo indicates the amount of total protein used per assay.
Figure 9:
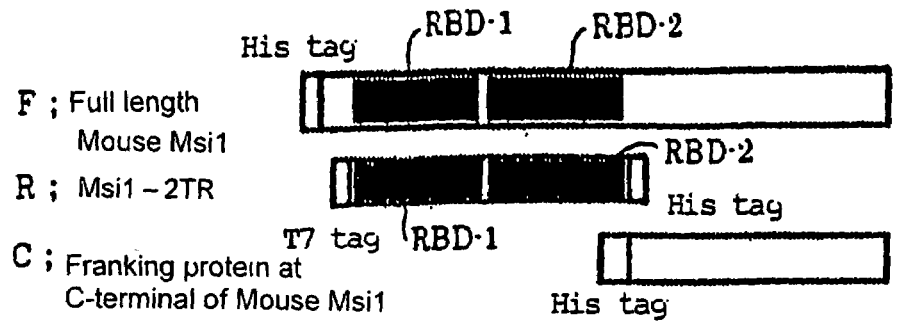
FIG. 9 is a schematic representation of Msi1 fusion proteins, in which F indicates full-length mouse Msi1, R represents a truncated protein containing two tandem RBDs (Msi1-2TR), and C designates a truncated protein containing C-terminal domain of mouse Msi1.
Figure 10:
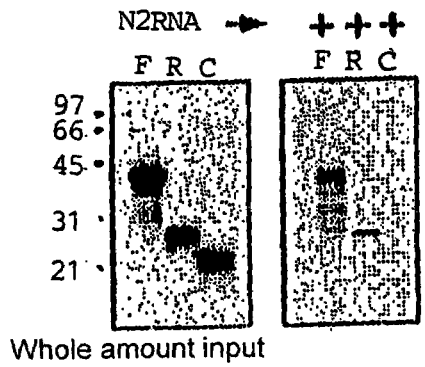
FIG. 10 shows binding of full-length Msi1 protein (F) and truncated Msi1-2TR protein (R, used for SELEX) with N2 RNA which contains a selected Msi1-binding sequence.

An examination was conducted as to whether Msi1 binds to the 3'-UTR of m-numb mRNA in vitro. For this purpose, various parts of m-numb mRNA were synthesized in vitro (N1, N2, N3) (FIG. 7) in the presence of biotin-14 CTP. A putative Msi1-binding site exists within N2. Three proteins, that is, the full-length Msi1 protein, a truncated protein containing two tandem RBDs of Msi1 (used for SELEX, Msi1-2TR), and a truncated protein containing the C-terminal portion of Msi1 were examined for their binding abilities to N2 (FIGS. 9 and 10). The full-length Msi1 protein and Msi-2TR were shown to bind to N2 under a moderate ionic strength condition that is close to the physiological condition (150 mM NaCl) (FIG. 10). [$^{35}$S]methionine-labeled full-length Msi1 protein coprecipitated with beads conjugated to N2, whereas the N1 and N2 portions of m-numb RNA did not interact with the full-length Msi1 protein (FIG. 8). UV cross-linking experiments showed that Msi1-2TR also binds to only N2, indicating that both full-length Msi1 and the truncated protein containing two tandem RBDs of Msi1

(Msi-2TR) preferentially bind to the N2 region within the 3'-UTR of m-numb mRNA in vitro. Thus, m-numb mRNA is a likely in vivo target of the Msi1 protein.

Figure 11:
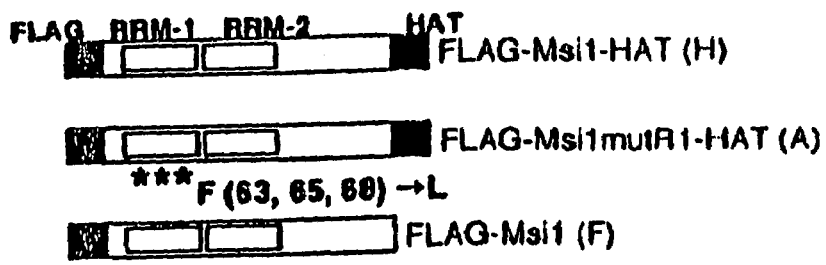
FIG. 11 illustrates schematic diagrams of Msi1 proteins FLAG-Msi1-HAT (H), FLAG-Msi1mutR1-HAT (A) and FLAG-Msi1 (F), in which the HAT tag at the C-terminal end is an affinity tag for Talon resin (Clontech) and FLAG-Msi1mutR1-HAT is a non-RNA-binding form of Msi1 with amino acid replacements in the N-terminal RNA-binding domain.
Figure 12:
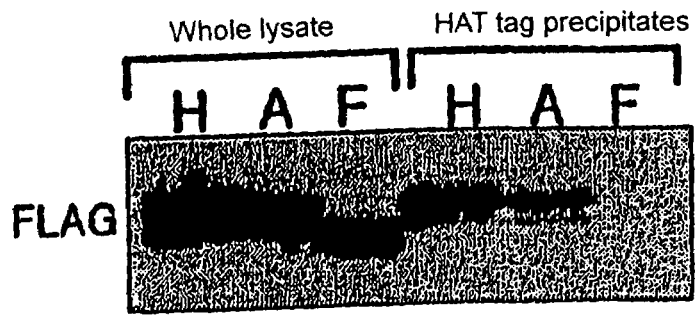
FIG. 12 depicts the results of analysis of expression of Msi1 proteins H, A and F in NIH 3T3 cells and HAT-tag-mediated affinity precipitation by immunoblotting with anti-FLAG monoclonal antibody.
Figure 13:
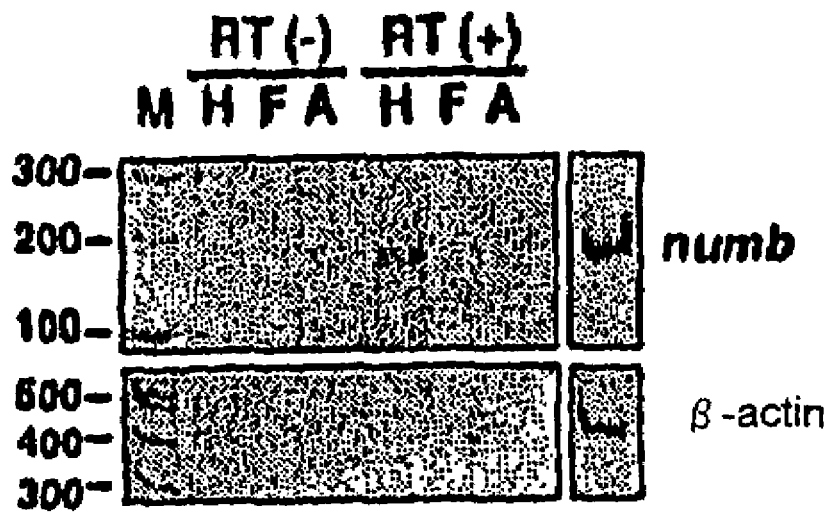
FIG. 13 shows the results of an in vivo RNA-binding assay combining RT-PCR and affinity precipitation, in which the RT(−) lanes were controls to ensure that the RT-PCR was RNA dependent, the right panels indicate an amplification control experiment to ensure primer fidelity using an RT product from an initial extract before incubation with an affinity resin (lanes H: FLAG-Msi1-HAT; lanes F: FLAG-Msi1; lanes A: FLAG-Msi1mutR1-HAT)

To determine whether Msi1 binds to the 3'-UTR of numb mRNA in vivo, we adopted a method reported in technical papers (Buckanovich et al., Mol. Cell. Boil., 17, 3194-3201, 1997; Levine et al., Mol. Cell. Biol., 13, 3494-3504; Steltz et al., Methods Enzymol., 180, 468-481, 1989). The Msi1-RNA complex was caused to precipitate from lysates of NIH 3T3 cells that had been transfected with a series of Msi1-expression vectors (FIG. 11). In NIH 3T3 cells, the m-numb gene is endogenously transcribed, while Msi1 is not expressed. The expression of HAT-tagged Msi1 protein (FIG. 12), which binds to Talon metal chelation affinity resin (Clontech) with high specificity in NIH 3T3 cells was induced (FIG. 12), and an examination was conducted as to whether the HAT-tagged Msi1 bound to m-numb mRNA. Cellular lysates from these transfected cells were applied to Talon metal chelation affinity resin (Clontech) to purify the Msi1-RNA complex. RNA that bound to the HAT-tagged Msi1 protein was then phenol extracted, reverse transcribed, and amplified by PCR using primers specific for m-numb or the abundantly expressed β-actin gene (used as an internal control). RNA that bound to the HAT-tagged Msi1 protein gave rise to reverse transcription (RT)-PCR product when the m-numb primers, but not the β-actin primers, were used (FIG. 13, lane H[RT(+)]). To prove the RNA-binding requirement of the Msi1 protein, a mutant Msi1 protein, FLAG-Msi1mutR1-HAT (FIG. 11), in which three aromatic amino acids that are essential for RNA binding had been replaced (63F→L, 65F→L, 68F→L), was also examined for its ability to bind endogenous m-numb RNA. As a result, the mutant Msi1 protein (FLAG-Msi1mutR1-HAT) failed to show binding to m-numb mRNA (FIG. 13, lane A), indicating that the retention of m-numb RNA on the affinity resin requires the RNA-binding ability of the Msi1 protein. As another control experiment, Msi1 protein without the HAT-affinity tag, FLAG-Msi1 (FIG. 11), was expressed in NIH 3T3 cells and the same binding assay was performed, which resulted in undetectable retention of m-numb mRNA on this resin (FIG. 13, lane F). These results demonstrate that Msi1 can interact with the endogenous m-numb RNA in vivo.

(4) Down-Regulation of m-numb Expression by Msi1 (Endogeneous m-Numb Expression and Reporter Assay)

Figure 14:
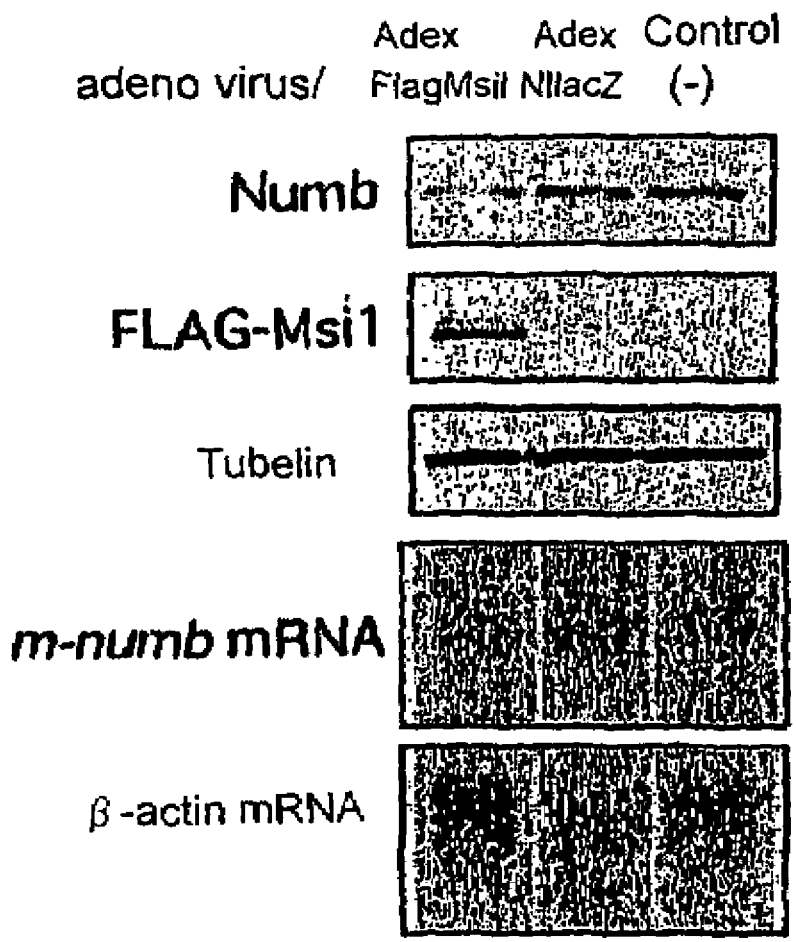
FIG. 14 illustrates recombinant adenovirus-mediated Msi1-misexpression, immunoblot analyses of m-Numb protein, and Northern blotting analysis.
Figure 15:
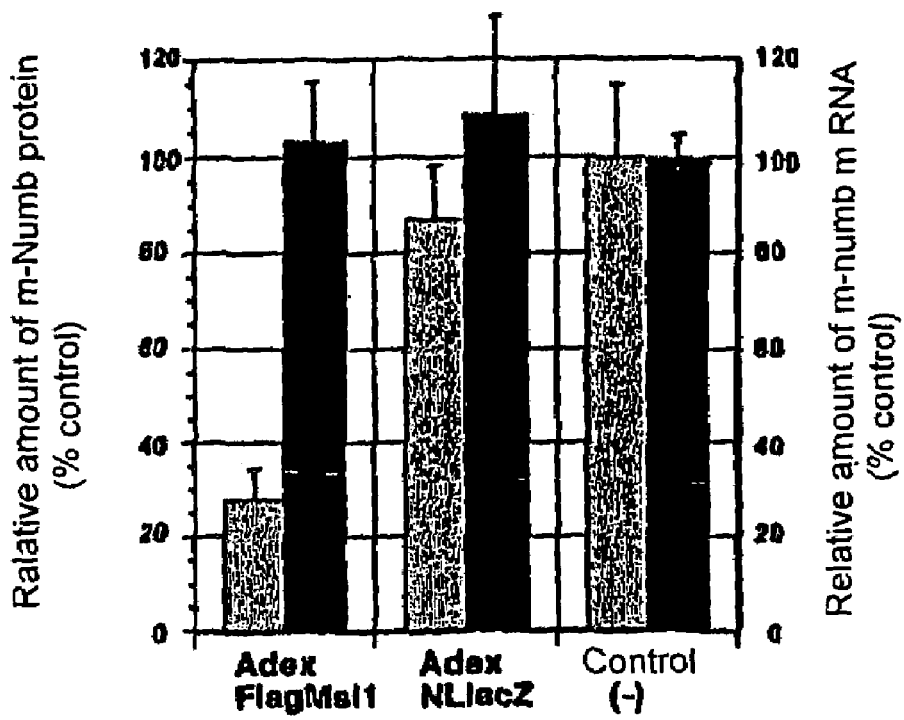
FIG. 15 is a schematic diagram depicting relative amounts of m-Numb protein (blank bar) and m-numb mRNA (filled bar)

To examine the effect of Msi1 protein on the expression of endogenous m-Numb protein, Msi1 was caused to misexpress in NIH 3T3 cells using a recombinant adenovirus vector (FIGS. 14 and 15). NIH 3T3 cells were infected with Adex-FLAGMsi1 or Adex-NLlacZ adenovirus under conditions that are not toxic to the cells. Infection with the Adex-FLAGMsi1 vector resulted in the expression of large amounts of FLAG-tagged Msi1 protein under the regulation of the CAG promoter, which is modified chicken β-actin promoter with the cytomegalovirus (CMV)1E enhancer. Since Msi1 expression did not alter the expression level of tubulin, tubulin was used as an internal control to assess the effect of Msi1 on the expression level of m-Numb protein. Msi1 overexpression decreased the level of the endogenous m-Numb protein to 32% of the level in control cells which expressed LacZ by infection with Adex-NLlacZ (FIGS. 14 and 15). However, the endogenous m-numb mRNA level remained unchanged in spite of the misexpression of Msi1 and LacZ (FIGS. 14 and 15). Based on these results, Msi1 protein is understood to inhibit the translational repression of m-Numb protein expression.

Figure 16:
FIG. 16 is a schematic representation of Msi1 effector and reporter constructs containing the 3'-UTR of m-numb (α: pcDNA3-T7msi1, β: pcDNA3-T7msi1mutR1 (α and β were under the control of the CMV promoter), a: pGVP2-numb3'-UTR, b: pGV-p2, C: pGVP2-reversed numb3'-UTR (a, b and c were under the control of the SV40 promoter)
Figure 16:
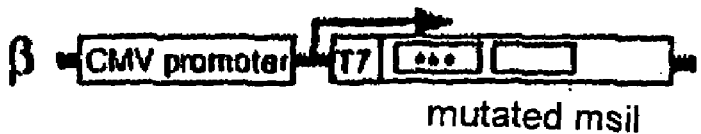
Figure 16:
Figure 16:
Figure 16:
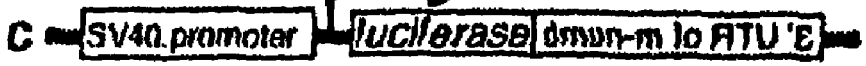
Figure 17:
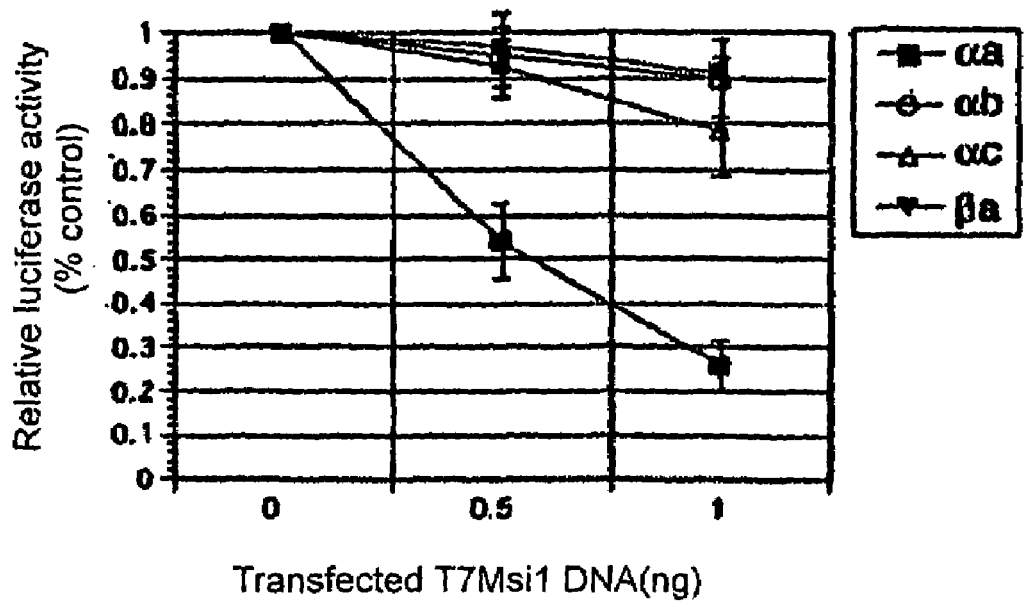
FIG. 17 is a schematic diagram illustrating a luciferase reporter assay.

Next, to investigate the mechanism of regulation by the Msi1 protein of the expression of its putative targets in vivo, a reporter assay system containing heterologous luciferase gene constructs was constructed. The firefly luciferase reporter plasmid and the Msi1 expression plasmid were transiently cotransfected into NIH 3T3 cells, in which Msi1 is not expressed endogeneously. The luciferase reporter gene combined with the 1.4-kb whole 3'-UTR of the m-numb gene was placed under the control of the SV40 promoter (FIG. 16). The expression level of the reporter gene was quantified by assaying the luciferase luminescence level. The wild-type msi1 gene and its non-RNA-binding variant (msi1mutR1) were driven under the control of the CMV promoter. As shown in FIG. 17, the level of luciferase enzymatic activity was reduced in the presence of exogenously expressed wild-type Msi1 in a dose-dependent manner. In contrast, Msi1mutR1, which lacks the RNA-binding activity did not (FIG. 17). Furthermore, wild-type Msi1 did not decrease the luciferase reporter activity, when the luciferase reporter gene lacked the m-numb 3'-UTR or was combined with the m-numb 3'-UTR in a reversed orientation to eliminate the Msi1-binding site (FIG. 17). Thus, the repression of the reporter gene expression was shown to be mediated by the RNA-binding activity of Msi1.

Figure 18:
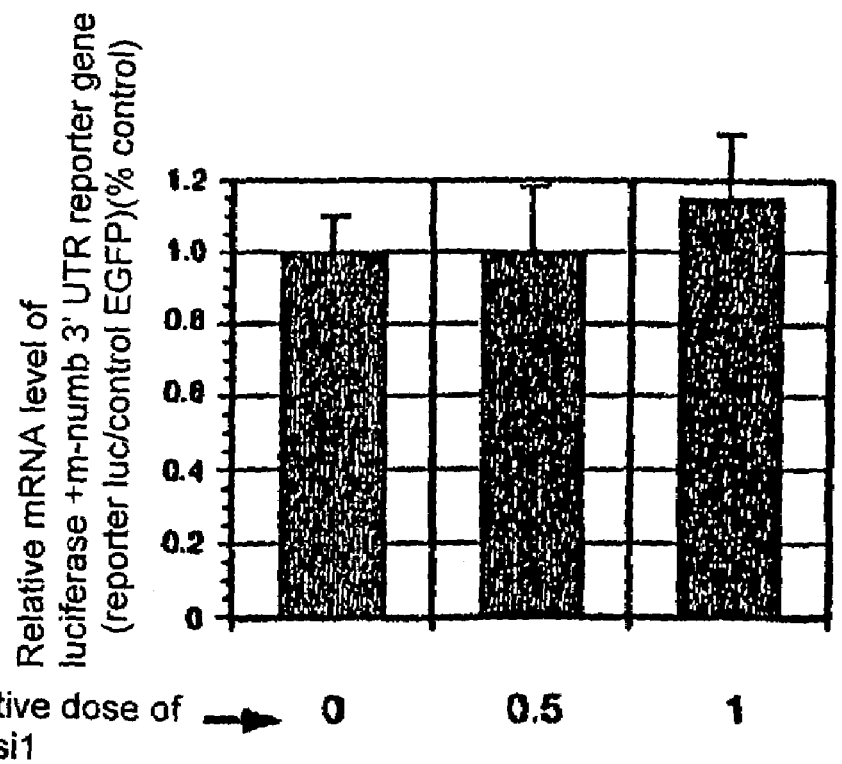
FIG. 18 depicts relative levels of reporter mRNAs quantified by Northern, in which the mRNA level of a transcript of EGFP, which does not contain an Msi1-binding site on its mRNA, was used as an internal control and the results were given as the ratios (percentages of control values) of reporter mRNA content to EGFP mRNA content (means and standard errors of the means of results from three independent experiments)

Furthermore, Msi1 appeared to translationally repress the expression of luciferase-m-numb 3'UTR chimeric reporter gene at the translational level, rather than by regulating the steady-state RNA level. RNA quantification using Northern blotting hybridization showed that increased levels of the msi1 gene product in NIH 3T3 cells did not affect the relative amount of reporter-numb 3'-UTR fusion mRNA in each experiment (FIG. 18).

Figure 19:
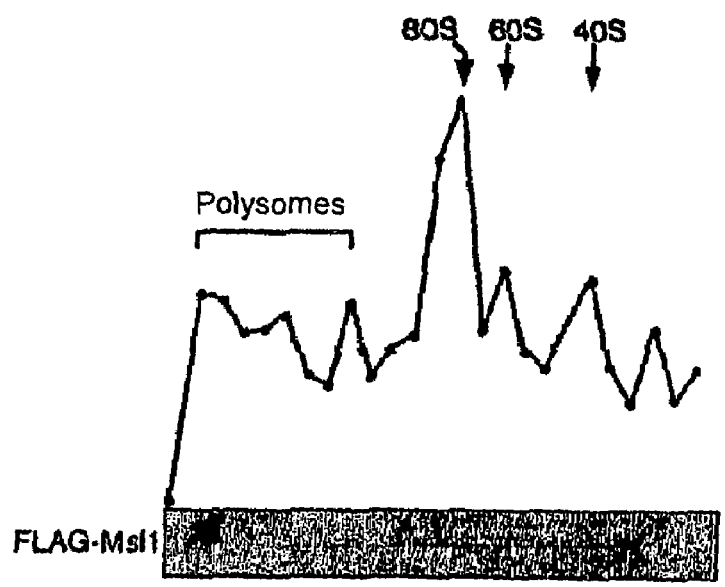
FIG. 19 shows a sucrose gradient profile of Msi1 protein containing ribosome particles in a cytoplasmic fraction of NIH 3T3 cells, in which the curve shows the $A_{254}$ of each fraction, the positions of 40S, 60S and 80S ribosomal particles and polysomes are indicated, and the lower panel shows the results of an immunoblot analysis of FLAG-Msi1 protein using anti-FLAG monoclonal antibody.

To further examine the possibility of translational repression by Msi1 protein, the subcellular localization of Msi1 protein was investigated by the fractionation of the cytoplasmic lysates of NIH 3T3 cells infected with Adex-FLAGMsi1 through the sedimentation on a linear sucrose gradient (5 to 30%). The $A_{254}$ of each fraction was used to observe ribosomes and ribosomal subunits as size markers. The assignment of ribosomal subunits was confirmed by extracting total RNA from each fraction. The presence of Msi1 protein was determined by Western blotting of each fraction with anti-FLAG monoclonal antibody. In the presence of 2 MM $MgCl_2$, Msi1 protein migrated to the position corresponding to those of polysome, 80S monosome, 60S ribosomal subunit, and 40S ribosomal subunits (FIG. 19). These findings demonstrate that Msi1 protein is associated with the ribosomes directly or indirectly.

Taken together, these observations indicated that m-numb mRNA is likely to be one of the in vivo targets of Msi1. Msi1 appears to translationally repress the expression of m-Numb protein through direct interaction with the 3'-UTR of m-numb mRNA.

(5) Potentiating Effect of Msi1 on Notch Signaling Activity

Figure 20:
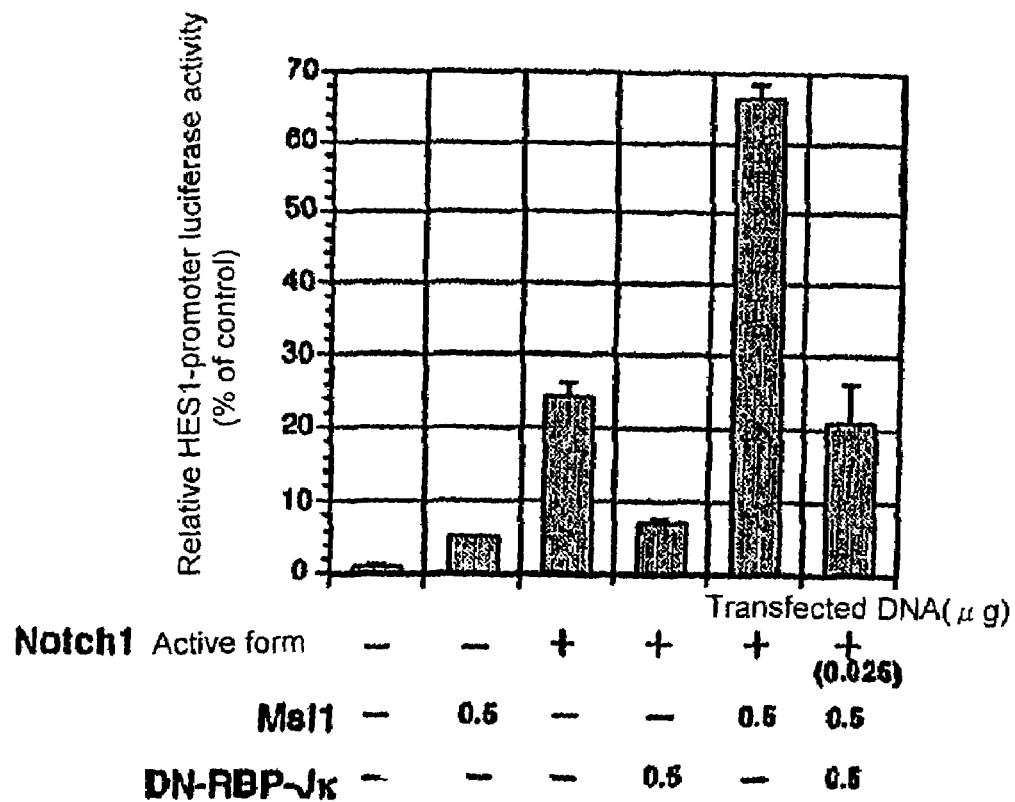
FIG. 20 depicts a correlation between Msi1 expression and Notch1-mediated activation of the HES1 promoter.
Figure 21:
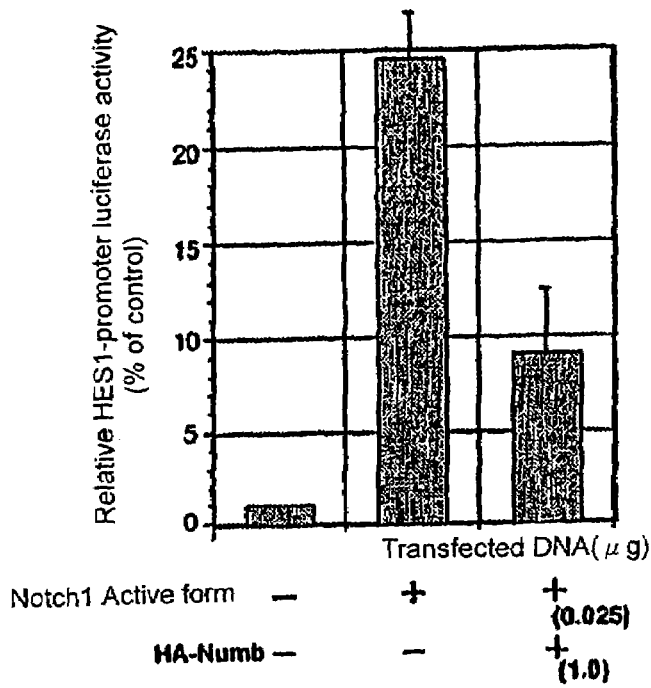
FIG. 21 illustrates a correlation between Numb misexpression and Notch1-mediated activation of the HES1 promoter.

To examine the biological significance of the translational repression of m-numb by the Msi1 protein, a luciferase reporter assay was performed using the HES1 promoter. The minimal HES1 promoter sequence, which has two RBP-$J_K$ binding sites, is transactivated when Notch signaling is induced. Transfection of Msi1 resulted in a slight increase of HES1 promoter activity (5.1-fold activation from the basal level)(FIG. 20). This slight up-regulation by Msi1 is likely to be attributed to the activation of endogenous Notch. An examination was conducted as to how the transactivating activity of the Notch1 intracellular domain (FCDN1), which is a dominant active form of Notch1, was modified by transfecting exogenous Msi1 into NIH 3T3 cells. Expression of the Notch1 active form alone resulted in a 24.5-fold activation of the HES1 promoter from the basal level (FIG. 20). This activation is inhibited by the expression of RBP-J$_K$ dominant negative form (R218H, designated DN-RBP-J$_K$ in FIG. 20), which has no binding site to the target DNA and blocks the activation of Notch signal. Furthermore, when exogeneous Msi1 expression was induced together with the Notch1 dominant active form, the HES1 promoter activity was up-regulated another 2.7-fold over the activation caused by the dominant active Notch1 alone (66-fold activation from the basal level (FIG. 20). The expression of Msi1 was found to potentiate the HES1 promoter activity synergistically with that of dominant active Notch1 (FIG. 20). The potentiation of HES1 promoter luciferase reporter activity by Msi1 is also suppressed by the expression of DN-RBP-J$_K$ (FIG. 20). Consequently, the induction of the HES1 promoter by Msi1 is likely to be due to the activation of Notch signaling through the DN-RBP-J$_K$-dependent pathway. On the other hand, transactivation of the HES1 promoter by Notch1 was found to be inhibited by misexpression of m-Numb protein (FIG. 21). Taken together, it has been demonstrated that misexpression of Msi1 in NIH 3T3 cells decreases the endogenous m-Numb protein level without affecting the mRNA level (FIGS. 14 and 15) and that m-Numb acts as an antagonist of Notch signaling in NIH 3T3 cells (FIG. 21). Thus, Msi1 is likely to be involved in activation of Notch-signaling through the RBP-J$_K$-dependent pathway by the translational repression of m-Numb.

(6) Antisense PNA msi 2 asPNA was one synthesized and purified by PE Biosystem in a manner known per se in the art. The sequence of msi2 asPNA is in conformity with the translation initiation codon (5' CTCCATAGCGGAGCC3'-Lys: SEQ ID NO: 11) or the coding region (5' ACCTAATACTTTATCT3'-Lys: SEQ ID NO: 12). To avoid self-association of PNA (Aidrian-Herrada et al., Nac. Acids. Res., 26, 615-621, 1998), lysine was added to the 3' terminus. These two asPNAs act likewise for the formation of neurospheres.

(7) Incubation of Neurospheres (Incubation of Neural Stem Cells)

Standard procedures of neurosphere formation and differentiation assay and preparation of a basal medium containing 20 ng/ml of EGF and 10 ng/ml of bFGF were conducted following the methods already mentioned above (Nakamura et al., J. Neurosci., 20, 283-293, 2000). Described specifically, cells of the front half of the telencephalon at E14.5 were used for the formation of primary spheres (5×10$^5$ cells/5 ml/well, 6-well plate) through self-renewal of neural stem cells. Upon separation the cells of the primary sphere into individual cells, msi2 asPNA was added in amounts (0 to 10 μm) shown in FIG. 24 to a culture medium, and the cells were transferred onto a secondary sphere forming plate (500 cells/200 μm/well, 96-well plate) and then incubated. On the fourth day after the subculture, the numbers of secondary spheres were counted, respectively. The cells for use in the semi-quantitative PT-PCR and immunocytochemical analysis of Msi2 were treated with 20 μM of mis2 asPNA for 24 hours and then harvested.

(8) Semi-Quantitative RT-PCR

Subsequent to the incubation for 24 hours with or without addition of msi2 asPNA, cells were harvested, respectively (1.5×10$^5$ cells). The total RNA, which had been isolated using the TRIzol reagent (Gibco-BRL), was treated with DNaseI (Gibco-BRL). After the first-strand cDNA was synthesized using SuperScript II reverse transcriptase (Gibco-BRL), treatment was conducted with RNase H (Takara). Using a primer set of msi2 (5' primer-5' GTCTGCGAACA-CAGTAGTGGAA' (SEQ ID NO: 13) and 3' primer5' GTAGCCTCTGCCATAGGTTGC3' (SEQ ID NO: 14'), 340 bp) and g3 pdh (5' primer5' ACCACAGTCCATGCCAT-CAC3' (SEQ ID NO: 15') and 3' primer5' TCCACCAC-CCTGTTGCTGTA3' (SEQ ID NO: 16), 452 bp), PCR was conducted by repeating, 35 or 38 cycles, denaturation with Extaq DNA polymerase (Takara) at 94° C. for 45 s, primer annealing at 54° C. for 1 min and DNA extension at 72° C. for 2 min. The amount of the template cDNA was normalized based on the amount of g3 pdh employed as an internal standard gene. Serially-diluted cDNA samples were amplified by repeating PCR 33 cycles with a g3 pdh primer set. Using cell samples independently prepared three times, the above-described experiment was performed three times. PCR products were separated by electrophoresis on a 5% polyacrylamide gel, and subsequent to staining with SYBR Green (Takara), visualization was effected using FMBIO II Multiview (Takara), followed by quantification.

Figure 22:
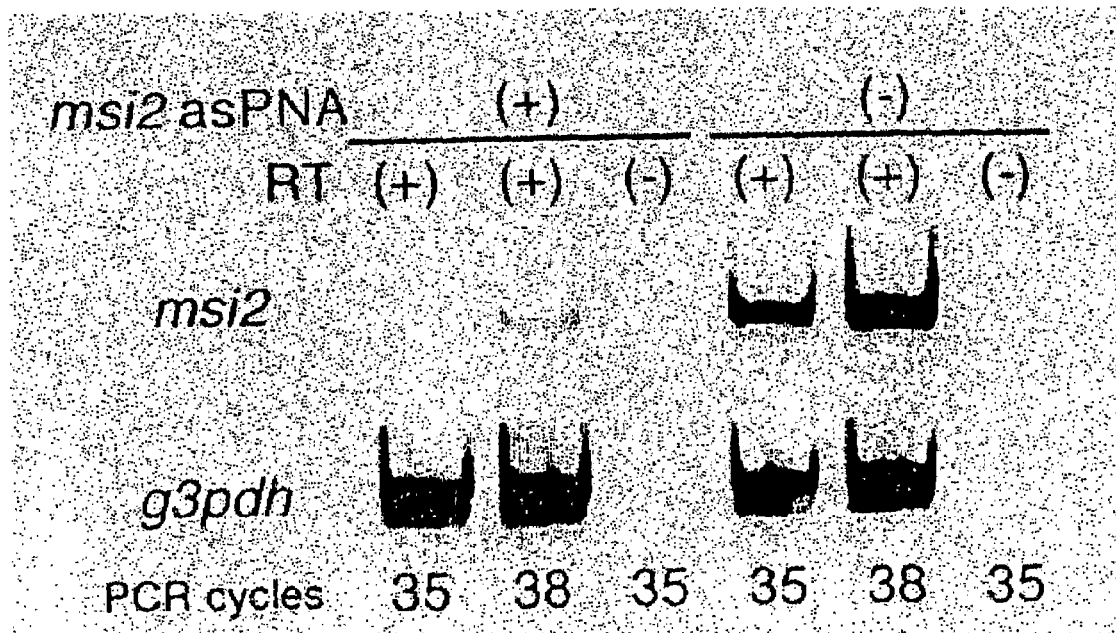
FIG. 22 is a schematic representation of the results of semi-quantitative RT-PCR analyses of msi2 and g3pdh mRNA, control, in the presence (+) or absence (−) of msi2 asPNA.
Figure 23:
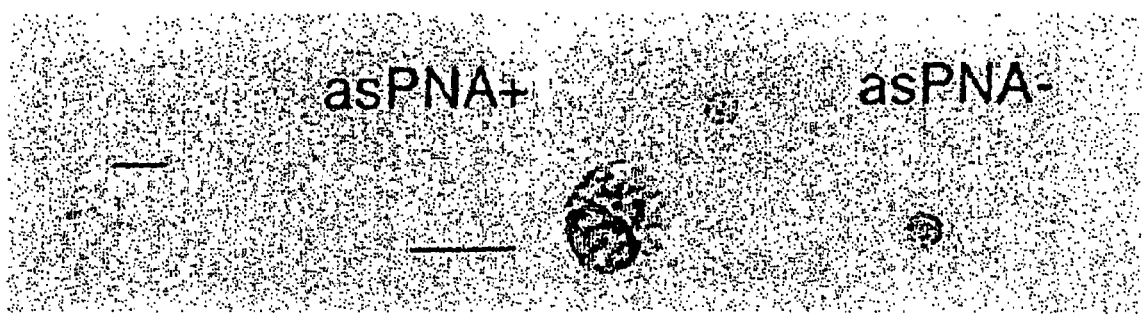
FIG. 23 is a photomicrograph representing the effects of msi2 asPNA on the expression of Msi2 protein visualized as immunoreactivities associated with anti-Msi2 antibody.
Figure 24:
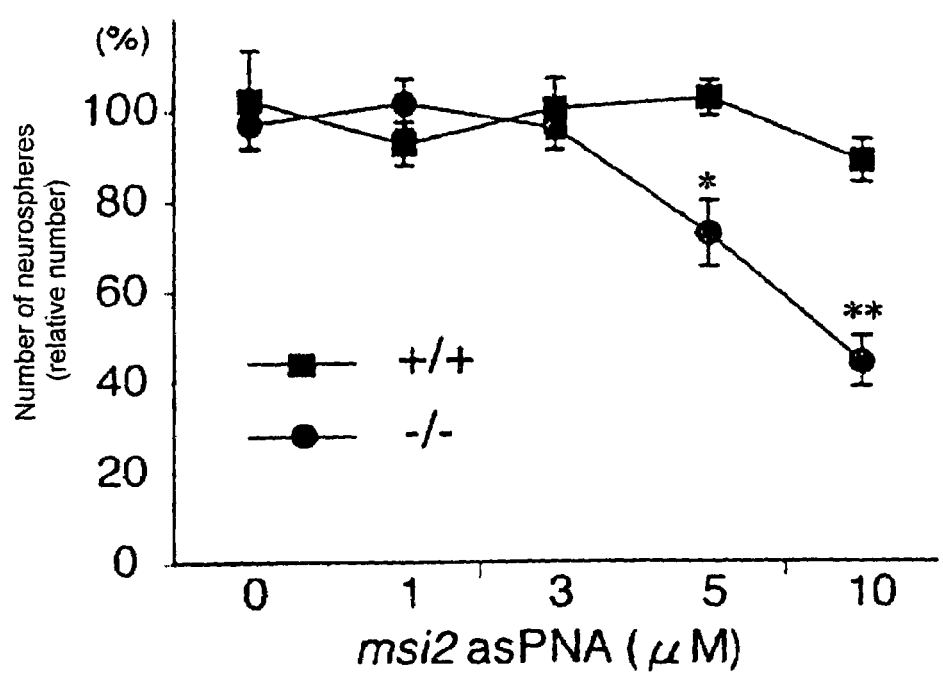
FIG. 24 is a schematic diagram illustrating results of a comparison in number of neurospheres formed by msi1$^{-/-}$ and those formed by a wild-type littermate, with the presence of msi2 asPNA.

To directly investigate participation of Msi family proteins on the function of CNS stem cells, double knock-out of two genes, Musashi1 and Musashi2, is considered to be meaningful. For this objective, an antisense compound which is specific for the msi2 gene was added to a culture of CNS stem cells prepared from an msi$^{-/-}$ embryo or a littermate, and the numbers of neurospheres obtained were counted. An antisense oligonucleotide of the translation initiation region or coding region (16 or 17 mer) of msi2 was synthesized as PNA (msi2 asPNA). PNA is a new-type structural homologue of DNA with a peptide of the same form contained as a skeleton, and therefore, has high sequence specificity to the target DNA and RNA, high stability to protease and nuclease, and further, low cytotoxicity. When msi2 asPNA is administered to incubated cells derived from the fetal animal forebrain, specific and pronounced reductions took place in the development of msi2 at both transcript and protein levels as demonstrated by semi-quantitative PT-PCR analysis and immunocytochemical detection on Msi2 antibody (FIGS. 22 and 23). When a neurosphere forming assay was performed on incubated msi1$^{-/-}$ cells in the presence of msi2 asPNA, a significant reduction in the formation of neurosphere was clearly observed in correlation to the dosage of msi2 asPNA (FIG. 24). In contrast to this, neurospheres were normally formed by wild-type incubated msi1$^{+/+}$ cells even in the presence of msi2 asPNA, resulting in the ascertainment of a finding that the neurosphere forming ability and survivability of wild-type CNS stem cells are not affected by repression of msi2 alone in the presence of msi2 asPNA of at least a certain specific concentration. Taking all the findings together, Msi1 and Msi2 both perform an important function in the proliferation and/or maintenance of embryonic CNS stem cells. This function is considered to be assigned to these two genes. In postnatal CNS stem cells, on the other hand, this function is considered to be performed primarily by Msi1 rather than Msi2.

INDUSTRIAL APPLICABILITY

The present invention has elucidated a new function of Musashi protein. Described specifically, Musashi protein inhibits expression of Numb protein having a neuronal differentiation regulating function and potentiates the activity of the Notch signaling system, so that Musashi protein can be used as a therapeutic for various diseases of the central nervous system and can also be used as a proliferation activity potentiator for neural stem cells.

The invention claimed is:

1. A method for potentiating neural stem cell proliferating activity, which comprises administering an effective amount of mammalian Musashi 1 protein to a mammalian subject by injection.

2. A method according to claim 1, wherein said injection is to the tissue or cells of said mammalian subject.

3. The method of claim 1, wherein said mammalian Musashi 1 protein is isolated from cells in which they are naturally expressed.

4. The method of claim 1, wherein said mammalian Musashi 1 protein is prepared by DNA recombination technology comprising transfected cells with an expression vector containing the cloned gene encoding for said mammalian Musashi 1 protein.

5. The method of claim 1, wherein said mammalian Musashi 1 protein is a mouse Musashi 1 protein.

6. The method of claim 1, wherein said mammalian Musashi 1 protein is isolated from mammalian CNS stem cells.

7. The method of claim 1, wherein said effective amount ranges from 0.1 µg to 10 mg per day in terms of the weight of the Musashi 1 protein.

8. The method of claim 1, wherein said neural stem cell proliferation is by inhibiting expression of Numb protein.

9. The method of claim 1, wherein said neural stem cell proliferation is by potentiating Notch signaling.

* * * * *

SEQUENCE LISTING

```
<160> NUMBER OF SEQ ID NOS: 18
<210> SEQ ID NO 1
<211> LENGTH: 45
<212> TYPE: DNA
<213> ORGANISM: Artificial Sequence
<220> FEATURE:
<223> OTHER INFORMATION: Primer for T7 promoter

<400> SEQUENCE: 1
cggaattcta atacgactca ctatagggaa gatctcgacc agaag          45

<210> SEQ ID NO 2
<211> LENGTH: 24
<212> TYPE: DNA
<213> ORGANISM: Artificial Sequence
<220> FEATURE:
<223> OTHER INFORMATION: Primer for T7 promoter

<400> SEQUENCE: 2
tgaggatcca tgtagacgca cata                                 24

<210> SEQ ID NO 3
<211> LENGTH: 23
<212> TYPE: DNA
<213> ORGANISM: Artificial Sequence
<220> FEATURE:
<223> OTHER INFORMATION: Primer for m-numb gene

<400> SEQUENCE: 3
atgagcaagc agtgttgtcc tgg                                  23

<210> SEQ ID NO 4
<211> LENGTH: 21
<212> TYPE: DNA
<213> ORGANISM: Artificial Sequence
<220> FEATURE:
<223> OTHER INFORMATION: Primer for m-numb gene

<400> SEQUENCE: 4
caagtagctg caactggctg g                                    21

<210> SEQ ID NO 5
<211> LENGTH: 27
<212> TYPE: DNA
<213> ORGANISM: Artificial Sequence
<220> FEATURE:
<223> OTHER INFORMATION: Primer for Beta-actin

<400> SEQUENCE: 5
cttcctccct ggagaagagc tatgagc                              27

<210> SEQ ID NO 6
<211> LENGTH: 24
<212> TYPE: DNA
<213> ORGANISM: Artificial Sequence
<220> FEATURE:
<223> OTHER INFORMATION: Primer for Beta-actin

<400> SEQUENCE: 6
gcctagaagc acttgcggtg cacg                                 24

<210> SEQ ID NO 7
<211> LENGTH: 22
<212> TYPE: DNA
```

-continued

```
<213> ORGANISM: Artificial Sequence
<220> FEATURE:
<223> OTHER INFORMATION: Primer for luciferase gene

<400> SEQUENCE: 7
gaggtcctat gattatgtcc gg                                              22

<210> SEQ ID NO 8
<211> LENGTH: 20
<212> TYPE: DNA
<213> ORGANISM: Artificial Sequence
<220> FEATURE:
<223> OTHER INFORMATION: Primer for luciferase gene

<400> SEQUENCE: 8
gttggagcaa gatggattcc                                                 20

<210> SEQ ID NO 9
<211> LENGTH: 19
<212> TYPE: DNA
<213> ORGANISM: Artificial Sequence
<220> FEATURE:
<223> OTHER INFORMATION: Primer for EGEP gene

<400> SEQUENCE: 9
cagaagaacg gcatcaagg                                                  19

<210> SEQ ID NO 10
<211> LENGTH: 20
<212> TYPE: DNA
<213> ORGANISM: Artificial Sequence
<220> FEATURE:
<223> OTHER INFORMATION: Primer for EGEP gene

<400> SEQUENCE: 10
tgctcaggta gtggttgtcg                                                 20

<210> SEQ ID NO 11
<211> LENGTH: 15
<212> TYPE: DNA
<213> ORGANISM: Artificial Sequence
<220> FEATURE:
<223> OTHER INFORMATION: msi2 asPNA

<400> SEQUENCE: 11
ctccatagcg gagcc                                                      15

<210> SEQ ID NO 12
<211> LENGTH: 16
<212> TYPE: DNA
<213> ORGANISM: Artificial Sequence
<220> FEATURE:
<223> OTHER INFORMATION: msi2 asPNA

<400> SEQUENCE: 12
acctaatact ttatct                                                     16

<210> SEQ ID NO 13
<211> LENGTH: 22
<212> TYPE: DNA
<213> ORGANISM: Artificial Sequence
<220> FEATURE:
<223> OTHER INFORMATION: primer for msi2 gene

<400> SEQUENCE: 13
gtctgcgaac acagtagtgg aa                                              22
```

<210> SEQ ID NO 14
<211> LENGTH: 21
<212> TYPE: DNA
<213> ORGANISM: Artificial Sequence
<220> FEATURE:
<223> OTHER INFORMATION: Primer for msi2 gene

<400> SEQUENCE: 14
gtagcctctg ccataggttg c                                        21

<210> SEQ ID NO 15
<211> LENGTH: 20
<212> TYPE: DNA
<213> ORGANISM: Artificial Sequence
<220> FEATURE:
<223> OTHER INFORMATION: Primer for g3pdh gene

<400> SEQUENCE: 15
accacagtcc atgccatcac                                          20

<210> SEQ ID NO 16
<211> LENGTH: 20
<212> TYPE: DNA
<213> ORGANISM: Artificial Sequence
<220> FEATURE:
<223> OTHER INFORMATION: Primer for g3pdh gene

<400> SEQUENCE: 16
tccaccaccc tgttgctgta                                          20

<210> SEQ ID NO 17
<211> LENGTH: 1551
<212> TYPE: DNA
<213> ORGANISM: mouse
<220> FEATURE:
<221> NAME/KEY: CDS
<222> LOCATION: (64)..(1152)

<400> SEQUENCE: 17

```
cgccgagcgc cgccgccgcc gccgccgccg ccgctccgct gcccgcgccg cccgcggctc      60 ccg atg gag act gac gcg ccc cag ccc ggc ctc gcc tcc ccg gac tcg       108
    Met Glu Thr Asp Ala Pro Gln Pro Gly Leu Ala Ser Pro Asp Ser
    1               5                  10                  15 ccg cac gac ccc tgc aag atg ttc atc gga gga ctc agt tgg cag acc       156
Pro His Asp Pro Cys Lys Met Phe Ile Gly Gly Leu Ser Trp Gln Thr
                20                  25                  30 acg cag gaa ggg ctg cgc gaa tac ttc ggc cag ttc ggg gag gtg aaa       204
Thr Gln Glu Gly Leu Arg Glu Tyr Phe Gly Gln Phe Gly Glu Val Lys
            35                  40                  45 gag tgt ctg gtg atg cgg gac ccc ctg acc aaa aga tcc agg ggt ttc       252
Glu Cys Leu Val Met Arg Asp Pro Leu Thr Lys Arg Ser Arg Gly Phe
        50                  55                  60 ggc ttc gtc act ttc atg gac cag gcg ggg gtg gat aaa gtg ctg gcg       300
Gly Phe Val Thr Phe Met Asp Gln Ala Gly Val Asp Lys Val Leu Ala
    65                  70                  75 caa tcg cgg cac gag ctc gac tcc aaa aca att gac ccc aag gtg gcc       348
Gln Ser Arg His Glu Leu Asp Ser Lys Thr Ile Asp Pro Lys Val Ala
80                  85                  90                  95 ttt cct cga aga gca cag cct aag atg gtc act cgg acg aag aag atc       396
Phe Pro Arg Arg Ala Gln Pro Lys Met Val Thr Arg Thr Lys Lys Ile
                100                 105                 110 ttc gtg ggg ggg ctg tct gtg aac acc acg gtg gaa gat gtg aaa cac       444
Phe Val Gly Gly Leu Ser Val Asn Thr Thr Val Glu Asp Val Lys His
```

```
              Phe Val Gly Gly Leu Ser Val Asn Thr Thr Val Glu Asp Val Lys His
                              115                 120                 125 tat ttc gag cag ttc gga aag gtg gat gat gcc atg ctg atg ttc gac         492
Tyr Phe Glu Gln Phe Gly Lys Val Asp Asp Ala Met Leu Met Phe Asp
        130                 135                 140 aaa acc acc aac agg cac aga ggg ttt gga ttt gtc acg ttt gag agc         540
Lys Thr Thr Asn Arg His Arg Gly Phe Gly Phe Val Thr Phe Glu Ser
145                 150                 155 gag gac atc gta gag aaa gtt tgt gag atc cac ttc cat gaa atc aac         588
Glu Asp Ile Val Glu Lys Val Cys Glu Ile His Phe His Glu Ile Asn
160                 165                 170                 175 aac aaa atg gtg gaa tgc aag aaa gcc cag cca aag gag gtg atg tcc         636
Asn Lys Met Val Glu Cys Lys Lys Ala Gln Pro Lys Glu Val Met Ser
                180                 185                 190 ccg aca ggc tca gcc cgg ggc agg tct cgg gtc atg ccc tac gga atg         684
Pro Thr Gly Ser Ala Arg Gly Arg Ser Arg Val Met Pro Tyr Gly Met
                195                 200                 205 gat gcc ttc atg ctg ggt att ggg atg ctg ggt tac cca ggg ttc caa         732
Asp Ala Phe Met Leu Gly Ile Gly Met Leu Gly Tyr Pro Gly Phe Gln
                210                 215                 220 gcc acg acc tac gcc agc cgg agt tac aca ggc ctt gcc cct ggt tac         780
Ala Thr Thr Tyr Ala Ser Arg Ser Tyr Thr Gly Leu Ala Pro Gly Tyr
        225                 230                 235 acc tac cag ttc ccc gaa ttc cgt gta gag cgg agc cct ctc ccg agc         828
Thr Tyr Gln Phe Pro Glu Phe Arg Val Glu Arg Ser Pro Leu Pro Ser
240                 245                 250                 255 gcc cca gtc ctc ccc gag ctc aca gct atc cct ctc acg gct tat ggg         876
Ala Pro Val Leu Pro Glu Leu Thr Ala Ile Pro Leu Thr Ala Tyr Gly
                260                 265                 270 ccc atg gcg gcg gca gcg gcg gcg gca gct gta gtt cga ggg aca ggc         924
Pro Met Ala Ala Ala Ala Ala Ala Ala Ala Val Val Arg Gly Thr Gly
                275                 280                 285 tct cac ccc tgg acg atg gct ccc cct cca ggt tcc act ccc agc cgc         972
Ser His Pro Trp Thr Met Ala Pro Pro Pro Gly Ser Thr Pro Ser Arg
                290                 295                 300 aca ggg ggc ttc cta ggg acc aca agc ccc ggc ccc atg gct gag ctc        1020
Thr Gly Gly Phe Leu Gly Thr Thr Ser Pro Gly Pro Met Ala Glu Leu
305                 310                 315 tac ggg gca gcc aac cag gac tcc ggg gtc agc agt tac atc agc gcc        1068
Tyr Gly Ala Ala Asn Gln Asp Ser Gly Val Ser Ser Tyr Ile Ser Ala
320                 325                 330                 335 gcc agc ccc gcc ccc agc act ggt ttc ggc cac agt ctt ggg ggt ccc        1116
Ala Ser Pro Ala Pro Ser Thr Gly Phe Gly His Ser Leu Gly Gly Pro
                340                 345                 350 ttg att gcc aca gcc ttc acc aat ggg tac cac tga aacagggagg             1162
Leu Ile Ala Thr Ala Phe Thr Asn Gly Tyr His
                355                 360 aggtagcagg agcgcccag cctgcagctg actgaggacc agactgagcc agcaagggga       1222
ttgggacacc tccgccgcag cagcccagcc ccttggctgc acttggacc gctactgcct       1282 gtccctcaac ccctgggccc agccccctca tgtctggctc cctactaac ctcctgttca       1342 gaccttgtct cttctctcgc tcccacctgc ctctctccct ggtcgctttt atttatttt       1402 ggattagcca gttgccctac ccccacacca gatctgccct ctcctccggt ctgccccatc     1462
cctccctgct gccccctta gggcaccccc ccccagaaa gcatagctg agggcgggc          1522 agaggggcc tgctgcagac tgaggcccc                                          1551

<210> SEQ ID NO 18
<211> LENGTH: 362
```

```
<212> TYPE: PRT
<213> ORGANISM: mouse

<400> SEQUENCE: 18

Met Glu Thr Asp Ala Pro Gln Pro Gly Leu Ala Ser Pro Asp Ser Pro
1               5                   10                  15

His Asp Pro Cys Lys Met Phe Ile Gly Gly Leu Ser Trp Gln Thr Thr
                20                  25                  30

Gln Glu Gly Leu Arg Glu Tyr Phe Gly Gln Phe Gly Glu Val Lys Glu
            35                  40                  45

Cys Leu Val Met Arg Asp Pro Leu Thr Lys Arg Ser Arg Gly Phe Gly
    50                  55                  60

Phe Val Thr Phe Met Asp Gln Ala Gly Val Asp Lys Val Leu Ala Gln
65                  70                  75                  80

Ser Arg His Glu Leu Asp Ser Lys Thr Ile Asp Pro Lys Val Ala Phe
                85                  90                  95

Pro Arg Arg Ala Gln Pro Lys Met Val Thr Arg Thr Lys Lys Ile Phe
            100                 105                 110

Val Gly Gly Leu Ser Val Asn Thr Thr Val Glu Asp Val Lys His Tyr
        115                 120                 125

Phe Glu Gln Phe Gly Lys Val Asp Asp Ala Met Leu Met Phe Asp Lys
130                 135                 140

Thr Thr Asn Arg His Arg Gly Phe Gly Phe Val Thr Phe Glu Ser Glu
145                 150                 155                 160

Asp Ile Val Glu Lys Val Cys Glu Ile His Phe His Glu Ile Asn Asn
                165                 170                 175

Lys Met Val Glu Cys Lys Lys Ala Gln Pro Lys Glu Val Met Ser Pro
            180                 185                 190

Thr Gly Ser Ala Arg Gly Arg Ser Arg Val Met Pro Tyr Gly Met Asp
        195                 200                 205

Ala Phe Met Leu Gly Ile Gly Met Leu Gly Tyr Pro Gly Phe Gln Ala
    210                 215                 220

Thr Thr Tyr Ala Ser Arg Ser Tyr Thr Gly Leu Ala Pro Gly Tyr Thr
225                 230                 235                 240

Tyr Gln Phe Pro Glu Phe Arg Val Glu Arg Ser Pro Leu Pro Ser Ala
                245                 250                 255

Pro Val Leu Pro Glu Leu Thr Ala Ile Pro Leu Thr Ala Tyr Gly Pro
            260                 265                 270

Met Ala Ala Ala Ala Ala Ala Ala Val Val Arg Gly Thr Gly Ser
        275                 280                 285

His Pro Trp Thr Met Ala Pro Pro Gly Ser Thr Pro Ser Arg Thr
    290                 295                 300

Gly Gly Phe Leu Gly Thr Thr Ser Pro Gly Pro Met Ala Glu Leu Tyr
305                 310                 315                 320

Gly Ala Ala Asn Gln Asp Ser Gly Val Ser Ser Tyr Ile Ser Ala Ala
                325                 330                 335

Ser Pro Ala Pro Ser Thr Gly Phe Gly His Ser Leu Gly Gly Pro Leu
            340                 345                 350

Ile Ala Thr Ala Phe Thr Asn Gly Tyr His
        355                 360
```